(12) United States Patent
Chang et al.

(10) Patent No.: US 7,033,458 B2
(45) Date of Patent: Apr. 25, 2006

(54) PROCESS FOR IMPROVING INTERFACIAL ADHESION IN A LAMINATE

(75) Inventors: Yihua Chang, Portland, OR (US); Richard L. Watkins, Portland, OR (US); David J. Goldwasser, Hillsboro, OR (US); Robert D. Thompson, Portland, OR (US); Richard P. Wool, Newark, DE (US)

(73) Assignee: Nike, Inc., Beaverton, OR (US)

( * ) Notice: Subject to any disclaimer, the term of this patent is extended or adjusted under 35 U.S.C. 154(b) by 65 days.

(21) Appl. No.: 10/137,531

(22) Filed: May 2, 2002

(65) Prior Publication Data

US 2002/0187289 A1 Dec. 12, 2002

Related U.S. Application Data

(63) Continuation-in-part of application No. 09/704,881, filed on Nov. 2, 2000.

(51) Int. Cl.
*B29O 65/00* (2006.01)
(52) U.S. Cl. .................... 156/309.6; 264/235; 264/346
(58) Field of Classification Search ............ 156/308.2, 156/308.4, 309.6, 309.9; 264/235, 346, 567
See application file for complete search history.

(56) References Cited

U.S. PATENT DOCUMENTS

| | | |
|---|---|---|
| 4,340,626 A | 7/1982 | Rudy |
| 4,936,029 A | 6/1990 | Rudy |
| 5,036,110 A | 7/1991 | Moureaux |
| 5,042,176 A | 8/1991 | Rudy |
| 5,713,141 A | 2/1998 | Mitchell et al. |
| 5,952,065 A | 9/1999 | Mitchell et al. |
| 6,013,340 A | 1/2000 | Bonk et al. |
| 6,082,025 A | 7/2000 | Bonk et al. |
| 6,124,007 A | 9/2000 | Wang et al. |
| 6,274,228 B1 * | 8/2001 | Ramesh et al. ............. 428/213 |

FOREIGN PATENT DOCUMENTS

WO WO 00/05067 * 2/2000

OTHER PUBLICATIONS

Wool, Richard P., Polymer Interfaces, "Strength of Incompatible Semicrystalline Interfaces," 1995, pp. 379-397.

* cited by examiner

*Primary Examiner*—Jeff H. Aftergut
*Assistant Examiner*—John L. Goff
(74) *Attorney, Agent, or Firm*—Harness, Dickey & Pierce, P.L.C.

(57) ABSTRACT

A method for improving adhesion between two adjacent layers of a laminate membrane includes annealing the laminate membrane at a temperature between an α-transition temperature and a β-transition temperature of at least one polymeric component of at least one of two adjacent layers for a time sufficient for the at least one polymeric component of at least one of the adjacent layers to partially diffuse into the other adjacent layer. A sealed, inflated bladder of the invention prepared from the laminate membrane can experience high strains without layer separation or peeling of the laminate layers, even at a seam.

24 Claims, No Drawings

PROCESS FOR IMPROVING INTERFACIAL ADHESION IN A LAMINATE

CROSS-REFERENCE TO RELATED APPLICATION

This application is a continuation-in-part of U.S. patent application Ser. No. 09/704,881 filed on Nov. 2, 2000, the disclosure of which is incorporated herein by reference.

FIELD OF THE INVENTION

This invention concerns methods for making laminate materials, particularly laminates having a layer including a thermoplastic elastomer adjacent to a layer including a polymeric barrier material.

BACKGROUND OF THE INVENTION

Laminate barrier membranes and inflatable bladders formed from such membranes have been used in a variety of products for inflation or cushioning, including vehicle tires, balls, accumulators used on heavy machinery, and in footwear. It is often desirable to use polymeric materials that are thermoplastic to form the membranes because thermoplastic materials may be reclaimed and reformed into new articles, reducing waste during manufacturing operations and promoting recycling after the life of an article. While thermoplastic barrier films may be flexed to a certain extent due to their thinness, thermoplastic barrier films having only layers of barrier material generally do not have sufficient elasticity for many applications, particularly for applications in which the inflated bladder is subjected to high strains during use. In order to overcome this problem, the barrier materials have been blended or layered with elastic materials. Elastic materials, or elastomers, are able to substantially recover their original shape and size after removal of a deforming force, even when the part has undergone significant deformation.

Known bladder barrier films that are composites or laminates, however, can also present a wide variety of problems in footwear bladders and other bladders that are subjected to high strains. In particular, such bladder laminates may experience layer separation and peeling. When such forces are applied to the pressurized bladder, the deformation of the bladder will exert shear forces at the interfaces of the laminate layers. Repeated deformation will fatigue the interface, resulting in interlaminar separation. Delamination is particularly acute if a seam is present in the construction. Thus, interfacial peel adhesion strength is a highly significant property for laminates used to form pressurized bladders that can experience high strains in use.

Some previously known multi-layer bladders used tie-layers or adhesives in preparing the multi-layer laminates to achieve interlayer bond strength high enough to avoid the delamination problems. The use of such tie layers or adhesives, however, generally prevents regrinding and recycling of any waste materials created during product formation back into an usable product, making manufacturing more expensive and producing more waste. The use of adhesives also increases the cost and complexity of preparing laminates. These and other perceived shortcomings of the prior art are described in more extensive detail in Rudy, U.S. Pat. Nos. 4,340,626; 4,936,029 and 5,042,176, each of which are hereby expressly incorporated by reference.

Another approach has been to react together the two distinct materials to form a grafted copolymer layer or a grafted copolymer at the interface of the layers of the two different materials. Moureaux, U.S. Pat. No. 5,036,110, incorporated herein by reference, is an example of a grafted copolymer composition. Moureaux discloses a resilient membrane for a hydropnuematic accumulator that includes a film of a graft copolymer of a thermoplastic polyurethane and an ethylene vinyl alcohol copolymer.

In an alternate approach, membrane laminates have been described that eliminate adhesive tie layers by providing membranes including a first layer of a thermoplastic elastomer, such as a thermoplastic polyurethane, and a second layer including a barrier material, such as a copolymer of ethylene and vinyl alcohol, wherein hydrogen bonding occurs over a segment of the membranes between the first and second layers. Such laminates with layers of flexible materials and layers of fluid barrier materials are described, for example, in U.S. Pat. No. 6,082,025, issued Jul. 4, 2000; U.S. Pat. No. 6,013,340, issued Jan. 11, 2000; U.S. Pat. No. 5,952,065, issued Sep. 14, 1999; and U.S. Pat. No. 5,713,141, issued Feb. 3, 1998, each of which is incorporated herein by reference. While the membranes disclosed in these references provide flexible, "permanently" inflated, gas-filled shoe cushioning components that are believed to offer a significant improvement in the art, still further improvements, particularly in improved interfacial adhesion, are offered by the present invention.

SUMMARY OF THE INVENTION

The present invention provides a method for improving the interfacial adhesion between two adjacent thermoplastic layers of a laminate membrane. The method includes at least a step of annealing the laminate membrane by heating the laminate membrane to a temperature above a thermal transition temperature of at least one polymeric component of one or both of the layers for a time sufficient for the at least one component to partially diffuse across the boundary into the adjacent layer. By "partially diffuse across the interfacial boundary into the adjacent layer" it is meant that a measurable amount of diffusion of that component into the adjacent layer has taken place. The diffusion across the interfacial boundary can be measured indirectly as an increase in peel strength of the membrane layers and can be examined by methods such as, for example, scanning electron microscopy and atomic force microscopy. Peel strength can be measured by the ASTM D 1876 T-peel test (with appropriate recognition that conditioning is unnecessary because no adhesive is used). In the preferred embodiments the peel strength may be increased at least 100%, more preferably at least 500%, above the peel strength obtained without the process of the invention.

The invention also provides a method having a step of annealing the laminate membrane by heating the laminate membrane to a temperature in the range from about the temperature at which an $\alpha$-peak occurs to about the temperature at which a $\beta$-peak occurs for at least one polymeric component of at least one of the layers.

The method may further include a step of forming the laminate from molten materials and may also include shaping the laminate with heat before or during the annealing step. Between the step or steps of forming and shaping the laminate and the annealing step there may also be a period of time, referred to herein as the "lag time," when the laminate is below the temperature at which significant diffusion across the interfacial boundary takes place. Alternatively, the annealing step may be carried out during or immediately after the step or steps of forming the laminate.

The present invention also provides a laminate material in which at least one component of at least one layer has partially diffused into an adjacent layer. In particular, the laminate membrane of the invention may have an interfacial adhesion strength of at least about 20 pounds per linear inch. A thermoplastic elastomer layer as one of the adjacent layers provides resiliency to a laminate membrane of the invention, while a barrier layer as the other of the adjacent layers allows the membrane to prevent the transfer of a fluid from one side of the membrane to the other. Such durable, elastomeric barrier membranes may be used to prepare inflated bladders. By "durable" it is meant that the membrane has excellent resistance to fatigue failure, which means that the membrane can undergo repeated flexing and/or deformation and recover without delamination along the layer interfaces of the membranes, preferably over a broad range of temperatures. For purposes of this invention, the term "membrane" is used to denote preferably a freestanding film separating a gas, preferably at higher than atmospheric pressure, from another fluid (liquid or gas) or from the gas at a lower pressure. Films laminated or painted onto another article for purposes other than separating fluids are preferably excluded from the present definition of a membrane.

A sealed, inflated bladder of the invention prepared from the laminate membrane can experience high strains without layer separation or peeling of the laminate layers, even at a seam. The invention further provides enclosures, including but not limited to permanently sealed, inflated bladders formed from the laminates of the invention, as well as articles containing such enclosures and bladders. The bladder may be inflated with a gas such as nitrogen, air, or a supergas, and used to inflate or cushion, for example sports balls or footwear. The term "supergas" refers to large molecule gases, such as $SF_6$, $CF_4$, $C_2F_6$, $C_3F_8$, and so on which are described in U.S. Pat. Nos. 4,183,156, Rudy et al, 4,287,250, Rudy, and 4,340,626, Rudy, incorporated herein by reference. The barrier membrane preferably has a gas transmission rate that is sufficiently low to allow the bladder to remain "permanently" inflated, that is, to retain a useful internal pressure for the useful life of the article into which it is incorporated. An accepted method for measuring the relative permeance, permeability, and diffusion of different film materials is ASTM D-1434. The gas transmission rate of a membrane is expressed at the quantity of gas per area per time that diffuses through the membrane. The gas transmission rate may be expressed in units of $cc/(m^2)(24\ hours)$.

DETAILED DESCRIPTION OF THE INVENTION

The present invention provides a method that includes at least a step of annealing a laminate membrane by heating the laminate membrane to above a thermal transition temperature of at least one polymeric component of one layer or of at least one polymeric component of each of two adjacent layers. The laminate membrane is annealed for a time sufficient for the at least one component to partially diffuse across the boundary into an adjacent layer. By "thermal transition temperature" it is meant the midpoint of a temperature transition region over which the polymeric component exhibits significant changes in properties. The thermal transition temperature may be a glass transition temperature or a crystalline melting temperature. Such thermal transitions are well-known and described in the literature. The thermal transition temperature of a particular polymeric component may be determined from references or determined experimentally by any of a number of known methods, including differential scanning calorimetry, differential thermal analysis, thermogravimetric analysis, dynamic mechanical analysis, and so on.

Preferably, the temperature of the annealing step is at least about 50° C., more preferably at least about 80° C., above the thermal transition temperature of at least one polymeric component of one or both of the layers. While higher temperatures reduce the amount of time at the annealing temperature needed to achieve optimum interfacial adhesion, the temperature should be below the flow temperature for the material of the layers to avoid deformation of the laminate membrane.

In a preferred embodiment, one of the laminate layers includes a crystalline material or a material having crystalline domains, and the laminate membrane is annealed by heating the laminate membrane to a temperature in the range from about the temperature at which segmental motion begins to occur to the temperature of onset of melting of the crystalline domains. For cooling of such materials, this temperature range would be described as the temperature region from the onset of crystallization to the temperature at which crystallization is complete. In crystalline or partially crystalline materials, these temperatures are $\alpha$-peak and $\beta$-peak transition temperatures.

The $\alpha$-peak and $\beta$-peak temperatures may be determined by dynamic mechanical analysis (DMA) as is known in the art. Other methods for determining the temperature range in which crystallization begins and ends for a given material include, without limitation, differential scanning calorimetry (DSC), for which scan rates and dynamic temperature oscillation can provide the onset, end point and kinetic dependence of crystallization; optical microscopy employing a photocell, which detects the decrease in optical transmission that occurs with onset of crystallization and continues to decrease as long as crystallization continues; nuclear magnetic resonance (NMR), which detects T1 relaxation times of atoms in the crystalline domains of the material; birefringence, which provides an optical stress factor that correlates to DMA measurements; and other known methods that measure properties sensitive to crystallinity of a material.

The laminate membrane is held at the annealing temperature for a time sufficient for the at least one component to partially diffuse into the adjacent layer. The diffusion across the interfacial boundary can be observed by scanning electron microscopy or other means, but the diffusion can also be conveniently measured indirectly as an increase in peel strength of the membrane layers. Peel strength can be measured by the ASTM D 1876 T-peel test (with appropriate recognition that conditioning is unnecessary because no adhesive is used). In preferred embodiments the peel strength is increased at least about 100%, more preferably at least about 200%, above the peel strength obtained without the process of the invention. In a more preferred embodiment, the peel strength is increased at least to about five times the peel strength than could be obtained without the annealing process.

In a particularly preferred embodiment, the annealing temperature is in the range from about the temperature at which segmental motion begins to occur in the crystalline domains to the melting temperature of the crystalline domains for a material of each of the adjacent layers. This situation results in diffusion or influx of material from each layer into the other, particularly when the crystallization rate of a first material diffusing from one layer differs from the crystallization of a second material diffusing from the second layer. The influx length, measured from the original interface to the farthest point of influx of material from the other layer, is preferably at least about 50 angstroms, more preferably at least about 100 angstroms, even more preferably at least about 200 angstroms, and generally may be up to about 1 micron.

In another preferred embodiment, the annealing is carried out at a temperature at which a first material of one layer is between its α-transition and β-transition and the material of second layer, into which the first material diffuses, has molten regions at the interface of the layers.

The laminate membrane should be exposed to the annealing temperature for at least about one minute, preferably at least about five minutes, more preferably at least about fifteen minutes, still more preferably at least about twenty minutes. In highly preferred embodiments, the laminate membrane is exposed to the annealing temperature for at least about thirty minutes, and especially for at least about forty minutes. The length of time that the laminate membrane is exposed to the annealing temperature may be quite long, but times longer than about two hours are commercially not preferred. Moreover, when the annealing temperature is high enough to risk deformation of the laminate membrane with longer exposure times, and the membrane has already been formed into its desired shape, then the time of exposure must accordingly be kept shorter. In general, the laminate membrane may be held at the annealing temperature for a length of time from about one minute to about two hours, preferably from about five minutes to about ninety minutes, and more preferably from about twenty minutes to about one hour. The amount of time and the temperature in the annealing step needed to achieve the desired results or maximum interlayer adhesion can be determined by straightforward testing and will depend on factors apparent to those of skill in the field, such as the thickness of each layer, the overall thickness of the laminate membrane, and the particular compositions of the layers. In general, thicker layers, thicker laminates, and higher molecular weight components would require longer times or higher temperatures. Higher temperatures above the thermal transition temperature, particularly temperatures above the β-transition temperature and especially temperatures near the α-transition temperature, as well as thinner layers and lower molecular weight components in general shorten the time necessary for annealing. The annealing time preferably maximizes the number of influxes and/or the length of influxes of the diffusing material into the other layer.

As an initial condition for the at least one component to partially diffuse across the boundary into the adjacent layer, the surface tensions of the polymer melts forming the laminate membrane layers should be sufficiently similar to allow wetting at the interface and adherence of the adjacent layers. Preferably, the polymers or polymer blends used to prepare the laminate membrane layers are selected so that the difference in surface tension between the polymer melts is no more than about 1.5 dynes/cm$^2$, and still more preferably the difference in surface tension between the two polymer melts is no more than about 1.0 dyne/cm$^2$. In addition, the more similar the solubility parameters or polarity of the diffusing component is to the solubility parameters or polarity of the material of the adjacent layer, the easier it is for the component to diffuse into the adjacent layer.

In a preferred embodiment, the laminate membrane includes, as adjacent layers, a thermoplastic elastomer layer and a thermoplastic gas barrier polymer layer. The thermoplastic elastomer layer provides elasticity and dimensional stability to the laminate and article made from the laminate.

The gas barrier polymer layer allows a closed container, such as a sealed bladder, formed from the laminate to retain an internal pressure of fluid, preferably gas. The thermoplastic elastomer layer will typically have an amorphous polymeric component having a glass transition temperature, while the thermoplastic gas barrier polymer layer will typically include a semi-crystalline polymeric component having a crystalline melting thermal transition associated with the crystalline regions as well as a glass transition temperature associated with the amorphous regions. The polymeric component or components that diffuse into the adjacent layer may be a polymer or may be a block unit of a block copolymer or grafted segment of a graft copolymer, such as a soft segment of a thermoplastic elastomer or a segment of a barrier copolymer material.

The thermoplastic elastomer layer includes at least one thermoplastic elastomer material. Thermoplastic elastomers in general have a soft or flexible segment or segments that provide elastomeric properties and hard or rigid segments acting as thermally reversible physical crosslinks that enable the polymer to be processed as a thermoplastic material while retaining elastic behavior at room temperature. For example, one kind of thermoplastic elastomer has one or more soft or rubbery polymer segments, such as a polyester or polyether segments, and hard or glassy polymer segments, such as polyurethane or polyurea segments. A-B-A block copolymers such as styrene/butadiene/styrene block copolymers have a similar structure, but the center of the polymer chain is always the soft or elastic segment (e.g., rubbery polybutadiene) while the ends are glassy (e.g., polystyrene). Another suitable class of thermoplastic elastomers are dynamic vulcanizates, in which a rubbery phase is vulcanized in a molten thermoplastic phase under shear.

Particular examples of useful thermoplastic elastomers include, without limitation, polyurethane-based elastomers prepared from polymeric polyols including polyurethanes prepared using polyester, polyether, and polycarbonate diols including polycaprolactone diols, polytetrahydrofuran diols, and polyester diols made from diols having eight or fewer carbon atoms and dicarboxylic acids having eight or fewer carbon atoms; flexible polyolefins; styrenic thermoplastic elastomers; polyamide elastomers; polyamide-ether elastomers; polymeric ester-ether elastomers; flexible ionomers; thermoplastic vulcanizates such as vulcanized EPDM in polypropylene; flexible poly(vinyl chloride) homopolymers and copolymers; flexible acrylic polymers; and combinations of these materials. Commercial materials include, without limitation, polyamide-ether elastomers marketed under the trademark PEBAX® by Elf Atochem, ester-ether elastomers marketed under the trademark HYTREL® by DuPont, ester-ester and ester-ether elastomers marketed under the trademark ARNITEL® by DSM Engineering, thermoplastic vulcanizates marketed under the trademark SANTOPRENE® by Advanced Elastomeric Systems, elastomeric polyamides marketed under the trademark GRILAMID® by Emser, elastomeric polyurethanes marketed under the trademark PELLETHANE® by Dow Chemical Company, Midland, Mich., ELASTOLLAN® polyurethanes marketed by BASF Corporation, Mt. Olive, N.J., TEXIN® and DESMOPAN® polyurethanes marketed by Bayer, MORTHANE® polyurethanes marketed by Morton, and ESTANE® polyurethanes marketed by B.F. Goodrich Co.

The thermoplastic elastomer layer in one embodiment includes a polyurethane elastomer prepared using a polyester polyol or a polyether polyol, particularly a polyester polyol. Preparation of such polyurethane elastomers is described in detail in U.S. Pat. No. 6,082,025, issued Jul. 4, 2000; U.S. Pat. No. 6,013,340, issued Jan. 11, 2000; U.S. Pat. No. 5,952,065, issued Sep. 14, 1999; and U.S. Pat. No. 5,713,141, issued Feb. 3, 1998, each of which has been incorporated herein by reference. Preferred polyester polyols for synthesizing the polyurethane elastomers have glass transition temperatures of at least about −100° C., preferably at least about −50° C., more preferably at least about −30° C., and even more preferably at least about −20° C. Preferred polyester polyols have glass transition temperatures of up to about 30° C., preferably up to about 10° C., and more preferably up to about −10° C. Polyester polyols having glass transition temperatures in the range from about −50° C. to about −10° C. are particularly preferred. The weight average molecular weight of the polyester polyol may be from about 500 to about 10,000, but preferably the polyester polyol has a weight average molecular weight of at least about 650, more preferably at least about 1000, and up to about 5000, more preferably up to about 4000, and even more preferably up to about 2000. Preparation of polyester polyols is well-known, and suitable reactants are described in the above patents. The polyester diol has a number average molecular weight of preferably at least about 300, more preferably at least about 500, and even more preferably at least about 750. The polyester diol may have a number average molecular weight of up to about 5000, more preferably up to about 2000, and even more preferably up to about 1500. In a preferred embodiment, the polyester diol has a number average molecular weight of from about 300 to about 5000, more preferably from about 500 to about 2000, and even more preferably from about 750 to about 2000. The number average and weight average molecular weights may be determined for example by ASTM D-4274.

Preferred polyester polyols include, without limitation, the hydroxyl-functional reaction products of one or more dicarboxylic acids or anhydrides of dicarboxylic acids, preferably aliphatic, having up to about 36 carbon atoms, preferably from about 2 to about 8 carbon atoms, and diols, preferably aliphatic diol, having from about 2 to about 12 carbon atoms, preferably from about 2 to about 8 carbon atoms, as well as the polymerization products of lactones such as γ-butyrolactone, δ-valerolactone, and ε-caprolactone and/or hydroxycarboxylic acids. Preferably the polymeric polyol is diol. Minor amounts of mono-functional, tri-functional, and higher functionality materials (perhaps up to 5 mole percent) can be included. Particular examples of suitable diols include, without limitation, ethylene glycol, diethylene glycol, triethylene glycol, propylene glycol, dipropylene glycol, butylene glycol, 1,3-propanediol, 1,4-butanediol, 1,6-hexanediol,1,3-butanediol, 2,3-butanediol, 1,3-pentanediol, 2,3-pentanediol, neopentyl glycol, 1,3-cyclopentanediol, 1,4-cylcohexanediol, 3,3-dimethyl-1,2-butanediol, 2-ethyl-2-methyl-1,3-propanediol, 2-methyl-2,4-pentanediol, 5-hexene-1,2-diol, 2-propyl-1,3-propanediol, pinacol, and so on; as well as combinations of these. A minor amount of a higher functionality polyol, such as trimethylolpropane or glycerol, preferably in an amount of less than about 5% by weight of the polyol, and more preferably less than about 2% of the polyol reactant. In a particularly preferred embodiment the polyester is linear, i.e., only diols are used.

Suitable dicarboxylic acids and anhydrides include, without limitation, oxalic acid, malonic acid, diglycolic acid, maleic acid, fumaric acid, citraconic acid glutaconic acid, itaconic acid, mesaconic acid, succinic acid, methylsuccinic acid, muconic acid, glutaric acid, adipic acid, pimelic acid, dimethylsuccinic acid, methylglutaric acid, cyclopentanedicarboxylic acid, butylmalonic acid, diethylmalonic acid, dimethylglutaric acid, methyladipic acid, ethylmethylsuccinic acid, and anhydrides thereof, as well as combinations of these acids and anhydrides. Preferred dicarboxylic acids include glutaric acid, succinic acid, malonic acid, maleic acid, and adipic acid, anhydrides thereof, and combinations of these acids and anhydrides.

In a preferred embodiment, the polyester is a polyester diol selected from polycaprolactone polyesters based on reaction of combinations of ε-caprolactone with an initiating diol such as ethylene glycol and polyesters prepared from ethylene glycol and/or 1,4-butanediol with adipic acid, glutaric acid, succinic acid, or anhydrides thereof or combinations of these acids.

The polyester-modified polyurethane may be formed by reaction of the polyester diol with at least one diisocyanate and, optionally, with one or more extender compounds (also called chain extension agents) having two isocyanate-reactive functionalities. The diisocyanate may be selected from aromatic, aliphatic, and cycloaliphatic diisocyanates and combinations thereof. Representatives of useful diisocyanates include, without limitation, m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4-diisocyanate, any of the isomers of hexahydrotoluene diisocyanate, isophorone diisocyanate, any of the isomers of hydrogenated diphenylmethane diisocyanate (methylene-bis-cyclohexyl isocyanate), naphthalene-1,5-diisocyanate, 1-methoxyphenyl-2,4-diisocyanate, any of the isomers of diphenylmethane diisocyanate, including 2,2'-diphenylmethane diisocyanate, 2,4'-diphenylmethane diisocyanate, and 4,4'-diphenylmethane diisocyanate, isomers of biphenylene diisocyanate including 2,2'-, 2,4'-, and 4,4'-biphenylene diisocyanates, 3,3'-dimethoxy-4,4'-biphenyl diisocyanate and 3,3'-dimethyl-diphenylmethane-4,4'-diisocyanate, isomers of tetramethylxylene diisocyanate (including m-TMXDI and p-TMXDI), xylylene diisocyanate, and combinations thereof. In one embodiment, the diisocyanate includes a diphenylmethane diisocyanate or mixtures of isomers thereof. Polyisocyanates having more than two isocyanate groups such as 1,2,4-benzene triisocyanate may be included at low levels, but it is preferred to use only diisocyanates.

Preferably, the reaction mixture of the polyester diol and the diisocyanate further includes one or more extender molecules that have two groups reactive with isocyanate functionality selected from active hydrogen-containing groups such as primary amine groups, secondary amine groups, thiol groups, and hydroxy groups. The molecular weights of the chain extenders preferably range from about 60 to about 400. Alcohols and amines are preferred. Useful examples of extender compounds include, without limitation, diols, dithiols, diamines, or compounds having a mixture of hydroxyl, thiol, and primary or secondary amine groups, such as aminoalcohols, aminoalkyl mercaptans, and hydroxyalkyl mercaptans. Particular examples of such materials include, without limitation, ethylene glycol, diethylene glycol, and higher polyethylene glycol analogs like triethylene glycol; propylene glycol, dipropylene glycol, and higher polypropylene glycol analogs like tripropylene glycol; 1,3-propanediol, 1,4-butanediol, 1,3-butanediol, 1,6-hexanediol, 1,7-heptanediol, neopentyl glycol, dihydroxyalkylated aromatic compounds such as 4,4'-isopropylidene diphenol, (bisphenol A), resorcinol, catechol, hydroquinone, benzenedimethanols, the bis (2-hydroxyethyl) ethers of hydroquinone and resorcinol; p-xylene-α,α'-diol; the bis (2-hydroxyethyl) ether of p-xylene-α,α'-diol; m-xylene-α,α'-diol and the bis (2-hydroxyethyl) and alkylene oxide adducts of such diols; diethyl toluene diamine, polyalkylpolyamines such as ethylenediamine, diethylenetriamine, and triethylenetetramine, difunctional polyoxyalkylene amines (available commercially from BASF Corporation or under the trademark JEFFAMINE® from Huntsman), methylenedianiline p-phenylenediamine, m-phenylenediamine, benzidine, 4,4'-methylenibis (2-chloroaniline), alkanolamines and alkylalkanolamines such as ethanolamine, propanolamine, butanolamine, methylethanolamine, ethylethanolamine, methylpropanolamine, tert-butylaminoethanol, and combinations thereof. Preferred extenders include ethylene glycol, diethylene glycol, triethylene glycol, tetraethylene glycol, propylene glycol, dipropylene glycol, tripropylene glycol, tetrapropylene glycol, 1,3-propylene glycol, 1,4-butanediol, 1,6-hexanediol, and combinations of these. In addition to the difunctional extenders, a small amount of trifunctional extenders such as trimethylol propane, 1,2,6-hexanetriol and glycerol, and/or monofunctional active hydrogen compounds such as butanol or dimethyl amine, may also be present. The amount of trifunctional extenders and/or monofunctional compounds employed is preferably 5.0 equivalent percent or less based on the total weight of the reaction product and active hydrogen containing groups employed.

The polyurethane preferably includes at least about 25 weight percent of the polyester diol. In a preferred embodiment, the polyurethane includes at least about 35 weight percent of the polyester segments, and it is even more preferred that the polyurethane includes at least about 40 weight percent of the polyester segments. The polyester-modified polyurethane may include up to about 80 weight percent of the polyester segments, preferably up to about 65 weight percent of the polyester segments, and even more preferably up to about 60 weight percent of the polyester segments. The polyester-modified polyurethane may include from about 25 to about 80 weight percent of the polyester segments, preferably from about 35 to about 65 weight percent of the polyester segments, and even more preferably from about 35 to about 55 weight percent of the polyester segments.

In general the ratio of equivalents of polyester diol to equivalents of extender compound(s) can be varied. Preferably, the ratio of equivalents of polyester diol to equivalents of extender is from about 1:1 to about 1:12, more preferably from about 1:1 to about 1:8. The ratio of equivalents of polyisocyanate, which is preferably all diisocyanate, to combined equivalents of polyester diol and extender ranges from about 0.96 to about 1.05 equivalent of isocyanate to 1 equivalent of the combined polyester diol and extender. More preferred is a range of from about 0.98 to about 1.04 equivalents of isocyanate per equivalent of combined polyester diol and extender and even more preferred is a range of about 1.001 to about 1.01 equivalent of isocyanate to 1 equivalent of the combined polyester diol and extender to prepare the elastomeric polyurethane.

The thermoplastic elastomer preferably has a weight average molecular weight of at least about 60,000, more preferably at least about 100,000. The thermoplastic elastomer also preferably has a weight average molecular weight of up to about 500,000, more preferably up to about 300,000.

The thermoplastic elastomer layer may include modifiers and additives in minor amounts. Examples of such modifiers and additives include, without limitation, plasticizers, fillers, pigments, dyes, light stabilizers, hydrolytic stabilizers, thermal stabilizers, antioxidants, rheology modifiers, organic anti-block compounds, fungicides, antimicrobials (including bacteriocides and the like), mold release agents, waxes such as Montan esters or bis-amide waxes, processing aids, and combinations of these. Transparent, substantially colorless membranes may be formed by omitting any colorants. Tinted transparent membranes may also be formed with transparent colorants. Inorganic fillers such as mica or talc may be included in amounts of up to about 40% by weight.

Examples of hydrolytic stabilizers include two commercially available carbodiimide based hydrolytic stabilizers known as STABAXOL P and STABAXOL P-100, which are available from Rhein Chemie of Trenton, N.J. Other carbodiimide- or polycarbodiimide-based hydrolytic stabilizers or stabilizers based on epoxidized soy bean oil may be useful. The total amount of hydrolytic stabilizer employed will generally be less than 5.0 wt. % of the composition's total.

Plasticizers can be included for purposes of increasing the flexibility and durability of the final product as well as facilitating the processing of the material from a resinous form to a membrane or sheet. By way of example, and without intending to be limiting, plasticizers such as those based on butyl benzyl phthalate (which is commercially available, e.g. as Santicizer 160 from Monsanto) have proven to be particularly useful. Regardless of the plasticizer or mixture of plasticizers employed, the total amount of plasticizer, if any, will generally be less than 20.0 wt. % of the total composition, typically less than about 5% by weight of the total composition.

The preferred laminate membrane also includes a polymeric barrier layer adjacent to the thermoplastic elastomer layer. The barrier layer includes at least one polymeric barrier material. Barrier layer materials typically form crystalline regions or spherulites that serve to make the egress of gas molecules through the layer more difficult. Examples of suitable polymeric barrier materials include, without limitation, ethylene-vinyl alcohol copolymers; vinylidene chloride polymer; acrylonitrile polymer; copolymers of acrylonitrile and methyl acrylate; semicrystalline polyesters, such as polyethylene terephthalate; polyamides, particularly semicrystalline nylons; crystalline polymers; epoxy resins based resorcinol and amines such as N,N-dimethylethylenediamine (DMDEA), JEFFAMINE® 600, 3-amino-n-propanol, and 4-amino-n-butanol; polyurethane engineering thermoplastics, such as the material available under the trademark ISOPLAST® from the Dow Chemical Company; and combinations of these materials. Preferably, the polymeric components of the barrier layer are all barrier materials.

Among preferred polymeric barrier materials are copolymers of ethylene and vinyl alcohol. Preferred copolymers of ethylene and vinyl alcohol have an average ethylene content of an amount from about 25 mole percent to about 48 mole percent. The polymeric barrier material is preferably an ethylene-vinyl alcohol copolymer having a weight average molecular weight of at least about 20,000 and also preferably has a weight average molecular weight of up to about 50,000. Commercial products are available under the name SORANOL from Nippon Gohsei Co., Ltd. and under the trademark EVAL® from the Evalca Company (Lisle, Ill.), a subsidiary of Kuraray Co., Ltd. (Osaka, Japan).

Among preferred ethylene-vinyl alcohol copolymers are those that have an α temperature to β temperature range of at least about 30° C., preferably at least about 40° C., and more preferably at least about 50° C. Suitable example of ethylene-vinyl alcohol copolymers are those having an α temperature to β temperature range of from about 150° C. to about 100° C., from about 160° C. to about 110° C., from about 170° C. to about 130° C., and from about 180° C. to about 130° C.

The barrier layer that is adjacent to the thermoplastic elastomer layer may include modifiers and additives in minor amount, including those mentioned above as suitable for the elastomer layer. Preferably, the polymeric components in the barrier layer are predominantly or essentially all polymeric barrier materials.

The annealing method is particularly useful when poor miscibility of the polymers of the adjacent laminate layers, as is true for the preferred thermoplastic elastomer/gas barrier polymer laminate membranes, limits the amount of entanglement at the laminate interface occurring during extrusion of the laminate.

The time required for diffusion across the boundary between the adjacent laminate layers is affected by the molecular weights of the polymeric components. Accordingly, the molecular weights of the polymeric components and the length of time for the heat annealing are dependent on one another; higher molecular weights require longer times. It is generally preferred to continue annealing until the peel strength between the adjacent layers would increase less than 10% if annealed for another hour.

The method may further include a step of forming the laminate membrane from molten materials. At least one thermoplastic elastomer layer and at least one adjacent barrier layer are used to form preferred laminates in the method of the present invention. In one preferred embodiment, the laminate membrane is formed with an inner layer of the barrier material composition adjacent on each side to a layer of thermoplastic elastomer. The barrier and thermoplastic elastomer layers can be alternated in additional layers as desired, for example as layers of elastomer-barrier-elastomer-barrier-elastomer to make a five-layer laminate membrane. Layers of other materials may also be included, particularly as the outermost layers. In one embodiment, a five-layer structure provides an innermost layer including an ethylene-vinyl alcohol copolymer, an intermediate layer including a thermoplastic polyurethane elastomer on each side of the innermost layer, and outer layers including a blend of ethylene-vinyl alcohol copolymer and thermoplastic elastomer, especially thermoplastic polyurethane elastomer, on each side of the laminate membrane.

While the laminate membrane prepared by the inventive process may be thin or thick, the laminate membrane should be thick enough to provide adequate wall strength and yet thin enough to provide adequate flexibility. Laminate membrane thicknesses from about 20 mils to about 70 mils are typical for blow molding operations. It is desirable for the barrier layer and the adjacent thermoplastic elastomer layer to each be at least about 0.4 mil thick, preferably at least about 0.5 mil thick, more preferably at least about 0.6 mil thick, and still more preferably at least about 1 mil thick; and for each of these layers to be up to about 3 mils thick, preferably up to about 2.5 mils thick, more preferably up to about 2 mils thick, and yet more preferably up to about 1.6 mils thick. When the laminate membrane has more than one barrier layer and/or more than one thermoplastic elastomer layer, each of these layers may have these thicknesses. In one embodiment, the laminate membrane has outer layers that are at least about 125 microns thick.

The membrane that is annealed may be a microlayer polymeric composite or include a layer of a microlayer polymeric composite. A microlayer polymeric composite has alternating thin layers of at least one fluid barrier material, as described above, and at least one elastomeric material, as described above. Also contemplated are microlayer polymeric composites that include layers of different fluid barrier materials and/or layers of different elastomeric materials, all of the different layers being arranged in regular repeating order. Other layers in addition to elastomeric layers and fluid barrier layers that alternate along with them in a regular, repeating order may optionally be included. Such microlayer polymeric composites and their use for forming inflated, sealed bladders and cushioning devices are described in Bonk et al., U.S. Pat. Nos. 6,127,026 and 6,082,025, the disclosures of each being incorporated herein by reference.

The microlayer polymeric composite should have at least about 10 layers. Preferably, the microlayer polymeric composite has at least about 20 layers, more preferably at least about 30 layers, and still more preferably at least about 50 layers. The microlayer polymeric composite can have thousands of layers, and the skilled artisan will appreciate that the number of layers will depend upon such factors as the particular materials chosen, thicknesses of each layer, the thickness of the microlayer polymeric composite, the processing conditions for preparing the multilayers, and the final application of the composite. The microlayer elastomer membranes preferably has from about 10 to about 1000 layers, more preferably from about 30 to about 1000 and even more preferably it has from about 50 to about 500 layers.

The average thickness of each individual layer of the fluid barrier material may be as low as a few nanometers to as high as several mils (about 100 microns) thick. Preferably, the individual layers have an average thickness of up to about 0.1 mil (about 2.5 microns). Average thicknesses of about 0.0004 mil (about 0.01 micron) to about 0.1 mil (about 2.5 microns) are particularly preferable. For example, the individual barrier material layers can be, on average, about 0.05 mils (about 1.2 microns). The thinner layers of the fluid barrier layer material improves the ductility of the bladder membrane.

The alternating layers of the elastomeric polymer and the fluid barrier polymer have their major surfaces aligned substantially parallel to the major surfaces of the composite. There are a sufficient number of layers of the fluid barrier polymer so that the microlayer composite has the desired fluid transmission rate.

The multilayer polymeric composites may be formed by at least two different methods. In a first process, the multilayer polymeric composites of the invention can be prepared using a two-layer, three-layer, or five-layer feed block that directs the layered stream into a static mixer or layer multiplier. The static mixer has multiple mixing elements, preferably at least about 5 elements, that increases the number of layers geometrically.

In a second method, the multilayer polymeric composites of the invention can be prepared by providing a first stream comprising discrete layers of polymeric material. A preferred embodiment of this method is described in detail in Schrenk, et al., U.S. Pat. No. 5,094,793, issued Mar. 10, 1992, which is incorporated herein in its entirety by reference. Briefly, the first stream comprising discrete layers can again be formed by directing the molten extrudate from extruders separately containing the elastomeric material and the fluid barrier material into a two-layer, three-layer, or five-layer feed block. The first stream is then divided into a plurality of branch streams, the branch streams are then redirected or repositioned and individually symmetrically expanded and contracted, being finally recombined in an overlapping relationship to form a second stream with a greater number of discrete layers. In addition, protective boundary layers may be incorporated according the method of Ramanathan et al., U.S. Pat. No. 5,269,995, issued Dec. 14, 1993, which is incorporated herein in its entirety by reference. The protective layers protect the structural and fluid barrier layers from instability and breakup during the layer formation and multiplication. The protective layers are provided by a steam of molten thermoplastic material which is supplied to the exterior surfaces of the composite stream to form a protective boundary layer at the wall of the coextrusion apparatus. The protective layer may add special optical or physical attributes to the microlayer polymeric composite material, such as special coloration, including metallic coloration obtained by including metallic or other flake pigments in the protective boundary layer.

Although it is not necessary for all of the layers to be complete layers, that is to extend in the plane of that layer to all edges of the piece, it is desirable for most layers to be substantially complete layers, that is to extend to the edges of the membrane.

The laminate membrane that is annealed in the method of the invention may be flat or may be formed into another shape. A flat film laminate may be prepared by coextrusion of the two or more layers of the laminate.

The method may also include a further step of forming the laminate into a shape with heat before the annealing step. In one embodiment, the laminate is formed into a shape by a blow molding process before the annealing step. In general, the bladders may be formed by a first step of coextruding the layers, or plies, in a laminate film of flat or tubular shape, then blow molding the film or tube into a desired final shape. For example, a liquefied elastomeric material and a liquefied polymeric barrier material may be co-extruded as a parison. A mold having the desired overall shape and configuration of the bladder is in position to receive the parison and is closed around the parison. The parison is cut at the edge of the mold. The mold is moved back to a position away from the extrusion die. The open portion of the parison above the mold is then fitted with a blow tube through which pressurized air or other gas, such as nitrogen, is provided. The pressurized air forces the parison against the inner surfaces of the mold. In a preferred embodiment, the membrane may be annealed while in the mold, either before or, preferably, after blowing, particularly at in the range between an $\alpha$ temperature and a $\beta$ temperature of one polymeric component of the membrane. The material is hardened in the mold to form a bladder having the preferred shape and configuration. The blown, shaped laminate is allowed to cool and harden in the mold, which may be at about 40° F. to 50° F., before it is removed from the mold. Meanwhile, a new mold is moved into place to accept the next section from the parison that has been cut away from the first mold.

Besides blow molding using continuous extrusion, the forming step may use intermittent extrusion by reciprocating screw systems, ram accumulator-type systems, or accumulator head systems; co-injection stretch blow molding; extruded or co-extruded sheet, blown film tubing, or profiles. Other forming methods include injection molding, vacuum molding, transfer molding, pressure forming, heat-sealing, casting, melt casting, RF welding and so on. The membrane may be annealed during heated forming steps, such as after drawing and vacuum forming the membrane to a desired shape, when the membrane may be held at an annealing temperature, particularly between an $\alpha$ temperature and a $\beta$ temperature of one polymeric component of the membrane.

The flat laminate or shaped laminate is then annealed as described above. In a preferred embodiment, the laminate is annealed at temperatures of up to about 100° C., more preferably up to about 140 or 150° C.

The laminate may be annealed immediately after it is extruded and/or formed, for example after it is removed from the mold if it is blow molded, or there may be a period of time between when the laminate is formed but before significant modulus building occurs in either the barrier or thermoplastic elastomer layer. While the lag time may vary according to the specific materials used, thickness of the layers in the laminate membrane, overall laminate thickness, typical lag times may be up to about 60 minutes, more preferably up to about 30 minutes, even more preferably up to about 20 minutes, and still more preferably up to about 15 minutes. The lag time generally should not be more than about two hours. When lag times are longer than about two hours, the modulus building referred to may prevent the laminate membrane from improving interfacial adhesion during the annealing step. Preferably, the lag time is not more than about 1.5 hours, more preferably not more than about one hour.

The multilayer polymeric composite membranes or membranes having one or more layers of multilayer polymeric composite may be annealed in the same way as the membranes having thicker layers. In one embodiment, the membrane may be annealed during a thermoforming step during a heating stage. In particular, after drawing and vacuum forming the membrane to a desired shape, the membrane may be held at an annealing temperature, particularly between an $\alpha$ temperature and a $\beta$ temperature of one polymeric component, before the laminate is cooled below the temperature at which annealing may take place.

In one preferred embodiment a laminate membrane, preferably having at least one polymeric gas barrier layer and at least one thermoplastic elastomer layer, is extruded. The extruded membrane is cooled to the desired annealing temperature. The rate of cooling to the annealing temperature is preferably up to about 50° C. per minute. The laminate membrane is then annealed according to the invention.

The present invention also provides a laminate material in which a component of one layer has partially diffused into an adjacent layer. In one preferred embodiment the laminate material of the invention has an interfacial adhesion strength of at least about 20 pounds per linear inch.

After the annealing step, the laminate may undergo further forming steps. For example, an annealed flat film may be cut into a desired shape. Two portions of the flat film may be sealed at the edges to form a bladder.

The invention further provides bladders, especially inflated bladders, including the laminates of the invention and articles including such bladders. The bladder may be inflated with a gas and permanently sealed. The laminate membranes of the invention having the annealed layers of thermoplastic elastomer layer adjacent to the layer of a polymeric gas barrier material offer flexibility and resistance to undesirable transmission of gases such as an inflationary gas. The durable, elastomeric membranes of the inflated bladders can be used in many applications, particularly for inflation or cushioning applications. By "durable" it is meant that the membrane has excellent resistance to fatigue failure, which means that the membrane can undergo repeated flexing and/or deformation and recover without delamination along the layer interfaces of composite barrier membranes, preferably over a broad range of temperatures.

The membranes, whether in the form of sheet, substantially closed containers, cushioning devices, accumulators or other structures, preferably will have a tensile strength on the order of at least about 2500 psi; a 100% tensile modulus of between about 350–3000 psi and/or an elongation of at least about 250% to about 700%.

In particular, the invention provides an inflatable bladder for inflation and cushioning, such as for inflating objects such as sports balls and cushioning in footwear or hydraulic accumulators. The bladder has a membrane that includes at least one layer of an elastomeric material, preferably a polyester-modified polyurethane material, and an adjacent layer of a polymeric barrier material. The membrane of the invention has elastomeric mechanical properties that allows it to repeatedly and reliably absorb high forces during use without degradation or fatigue failure. It is particularly important in these kinds of applications for the membrane to have excellent stability in cyclic loading. The barrier membrane has a low gas transmission rate that allows it to remain inflated, and thus provide cushioning or inflation, for substantially the expected life of the article without the need to periodically re-inflate and re-pressurize the bladder; thus it may be permanently sealed.

The inflatable bladders may provide inflation and cushioning in a broad range of applications, including but not limited to bladders for inflatable objects such as balls, including footballs, basketballs, and soccer balls; inner tubes; flexible floatation devices such as tubes or rafts; as a component of medical equipment such as catheter balloons; as part of an article of furniture such as chairs and seats, as part of a bicycle or saddle, as part of protective equipment including shin guards and helmets; as a supporting element for articles of furniture and, more particularly, lumbar supports; as part of a prosthetic or orthopedic device; as a portion of a vehicle tire, particularly the outer layer of the tire; and as part of certain recreation equipment such as components of wheels for in-line or roller skates. Accumulators, and more particularly, hydraulic accumulators are used for vehicle suspension systems, vehicle brake systems, industrial hydraulic accumulators or for other applications having differential pressures between two potentially dissimilar fluid media. The laminate membrane separates the hydraulic accumulator into two chambers or compartments, one of which contains a gas such as nitrogen and the other one of which contains a liquid. Footwear is another important application for the inflatable bladders.

Footwear, and in particular shoes, usually include two major components, a shoe upper and a sole. The general purpose of the shoe upper is to snugly and comfortably enclose the foot. Ideally, the shoe upper should be made from an attractive, highly durable, comfortable materials or combination of materials. The sole, constructed from a durable material, is designed to provide traction and to protect the foot during use. The sole also typically serves the important function of providing enhanced cushioning and shock absorption during athletic activities to protect the feet, ankles, and legs of the wearer from the considerable forces generated. The force of impact generated during running activities can amount to two or three times the body weight of the wearer, while other athletic activities such as playing basketball may generate forces of between six and ten times the body weight of the wearer. To provide these functions, the sole typically has a midsole or insole having cushioning and an outsole having a traction surface.

The cushioning bladders of the invention are useful in the midsole or insole of a shoe. One type of sole structure with appropriate impact response is soles, or inserts for soles, that contain a bladder element containing either a liquid or, preferably, a gaseous fluid. The bladder elements are either encapsulated in place during formation of a foam midsole or cemented in a shallow cavity of a foam midsole, usually with a separate piece of foam cemented on top. Such resilient, shock absorbent materials or components may also be applied to the insole portion of a shoe, which is generally defined as the portion of the shoe upper directly underlining the plantar surface of the foot.

In cushioning components for footwear and other uses, the membranes preferably are capable of containing a captive gas for a relatively long period of time. In a highly preferred embodiment, for example, the membrane should not lose more than about 20% of the initial inflated gas pressure over a period of approximately two years. In other words, products inflated initially to a steady state pressure of between 20.0 to 22.0 psi should retain pressure in the range of about 16.0 to 18.0 psi for at least about two years.

The bladder or cushioning device may be inflated with air or components of air such as nitrogen, or with supergases. When used as cushioning devices in footwear such as shoes, the bladder may be inflated, preferably with nitrogen, to an internal pressure of at least about 3 psi, preferably at least about 5 psi, and up to about 50 psi. Preferably the bladder is inflated to an internal pressure from about 5 psi to about 35 psi, more preferably from about 5 psi to about 30 psi, still more preferably from about 10 psi to about 30 psi, and yet more preferably from about 10 psi to about 25 psi. It will be appreciated by the skilled artisan that in applications other than footwear applications the desired and preferred pressure ranges may vary dramatically and can be determined by those skilled in that particular field of application. Accumulator pressures, for example, can range up to perhaps 1000 psi. Accumulator pressures are preferably up to about 500 psi. A preferred range of pressure for accumulator applications is from about 200 psi to about 1000 psi, but pressures as low as about 25 psi are possible depending upon the design of the accumulator. After being inflated, the inflation port may be sealed, for example by RF welding, for a permanently sealed inflated bladder.

For the bladders to remain permanently inflated, the gas transmission rate must be suitably low. In one preferred embodiment, the membrane of the bladder has a gas transmission rate toward the inflationary gas, which is preferably air or nitrogen gas, should be less than about 15 cubic centimeters per square meter per atmosphere per day (cc/$m^2$·atm·day), preferably less than about 6 cc/$m^2$·atm·day, particularly less than about 4 cc/$m^2$·atm·day, more preferably less than about 2.5 cc/$m^2$·atm·day, yet more preferably less than about 1.5 cc/$m^2$·atm·day, and particularly preferably less than about 1 cc/$m^2$·atm·day. An accepted method of measuring the relative permeance, permeability, and diffusion of different film materials is set forth in the procedure designated as ASTM D-1434. While nitrogen gas is the preferred captive gas for many embodiments and serves as a benchmark for analyzing gas transmission rates in accordance with ASTM D-1434, the membranes can contain a variety of different gases and/or liquids.

The invention is further described in the following examples. The examples are merely illustrative and do not in any way limit the scope of the invention as described and claimed. All parts are parts by weight unless otherwise noted.

EXAMPLES

Bladders were blow molded using a layer of EVAL® F101 ethylene-vinyl alcohol copolymer (EVOH) (available from Evalca Company, Lisle, Ill.) and layers of a blend of 3% by weight of F101 in PELLETHANE® 2355-80AE polyurethane (available from the Dow Company, Midland, Mich.), processed at 215° C., adjacent to the EVOH layer on either side.

In Example 1, the bladder was removed from the mold and, after a lag time of six minutes, placed in a 140° C. convection oven for 20 minutes. The EVAL® F101 EVOH has an α temperature of 180° C. and β temperature of 130° C.

The Comparative Example A was not annealed.

A one inch-wide strip was cut from each bladder for testing interfacial adhesion between the layers. The strips were cut crosswise to the barrier layer using a razor blade. The barrier layer had two interface surfaces, an inside interface that was air-cooled on the inside of the parison and an outside interface that was mold-cooled from the outside of the parison. To test the interfacial adhesion, one polyurethane layer was pulled away from the barrier layer to allow grips from a tensile tester to grasp the polyurethane layer and, separately, the other side of the test strip containing both the barrier layer and other polyurethane layer. Once the sample was placed in the tensile grips, the crosshead was activated at 2"/min. A transducer attached to the stationary grips recorded the force needed to continue pulling the separated polyurethane layer from the barrier interface uniformly across the 1" wide strip. When the peel force leveled off, the test was halted and the force per lineal inch was recorded.

Peel forces were recorded for both the inside and outside interface of the bladder.

| EXAMPLE | INSIDE PEEL ADHESION (pounds per lineal inch) | OUTSIDE PEEL ADHESION (pounds per lineal inch) |
|---|---|---|
| A | 4.0 | 5.2 |
| 1 | 17.6 | 17.6 |

Example 2

A sealed, inflated bladder is formed from the annealed, blow molded bladder prepared according to Example 1 by die trimming the excess flash from around the part. The die-trimmed part is inserted into an inflation machine. A needle that fits into the molded blow hole is automatically inserted. Nitrogen gas fills the bladders until a designated pressure is reached. The bladder is then provided with multiple chambers having different pressures by closing An RF around the inflation tube and applying RF energy for sufficient time to melt the polymer and seal the path. More gas is then added to the bladder until the next highest pressure is attained. At this point another set of RF dies comes down on another inflation tube to RF seal the pathway. The procedure is repeated until all unique pressure chambers in the bladder have been filled and sealed.

Example 3

A shoe is prepared from the sealed, inflated bladder of Example 2 by first cleaning and drying the inflated bladder. The bladder is then sprayed with a primer coat and dried. The top and bottom are painted to provide color, then air dried. To put the shoe together, the bladder and an outsole inserted into a mold and a TPU foam is molded and cured around the bag and over the outsole. A pre-stitched upper is glued to this midsole/outsole assembly under pressure and cooled in an air tunnel.

The invention has been described in detail with reference to preferred embodiments thereof. It should be understood, however, that variations and modifications can be made within the spirit and scope of the invention.

What is claimed is:

1. A method for improving adhesion between two adjacent layers of a laminate membrane, comprising the steps of:
   (a) forming a laminate having a first thermoplastic layer adjacent to a second thermoplastic layer and having an interfacial boundary between the first thermoplastic layer and the second thermoplastic layer;
   (b) after a lag time when the laminate is below a temperature at which significant diffusion across the interfacial boundary takes place, annealling the laminate at least one temperature between an α-transition temperature and a β-transition temperature of at least one polymeric component of at least one of the layers for a time sufficient for the at least one polymeric component to partially diffuse into the adjacent layer.

2. A method according to claim 1, wherein the laminate is shaped with heat during the annealing step.

3. A method according to claim 1, wherein the annealing step takes place immediately after a step of forming the laminate into a desired shape.

4. A method according to claim 1, wherein the annealing step is carried out for a time sufficient to produce an interfacial adhesion strength of at least about 20 pounds per linear inch.

5. A method according to claim 1, wherein one of the layers has a semi-crystalline polymer and the annealing step (b) is carried out at one or more temperatures between an α-transition temperature and a β-transition temperature of the semi-crystalline polymer.

6. A method according to claim 1, wherein the annealing step (b) increases the peel strength between the layer and the adjacent layer by at least about 100%.

7. A method according to claim 1, wherein the annealing step (b) increases the peel strength between the layer and the adjacent layer by at least about 500%.

8. A method according to claim 1, wherein the laminate has at least three layers and further wherein during the diffusion occurs at two or more interfaces between layers.

9. A method according to claim 1, wherein a polymeric material of the adjacent layer has molten regions at the annealing temperature or temperatures.

10. A method according to claim 1, wherein the annealing step (b) is carried out for a time sufficient that the peel strength between the layer and the adjacent layer would increase less than 10% if annealed for another hour.

11. A method according to claim 1, wherein the polymeric component comprises a thermoplastic gas barrier polymer and the adjacent layer comprises a thermoplastic elastomer.

12. A method according to claim 11, wherein the thermoplastic elastomer comprises a material selected from the group consisting of polyurethanes prepared using polyester, polyether, and polycarbonate diols, flexible polyolefins, styrenic thermoplastic elastomers, polyamide elastomers, polyamide-ether elastomers, polymeric ester-ether elastomers, flexible ionomers, thermoplastic vulcanizates, vulcanized EPDM in polypropylene, flexible poly(vinyl chloride) homopolymers and copolymers, flexible acrylic polymers, and combinations thereof.

13. A method according to claim 11, wherein the thermoplastic elastomer comprises a polyurethane prepared form a polyester diol.

14. A method according to claim 11, wherein the thermoplastic gas baffler polymer comprises a material selected from the group consisting of ethylene-vinyl alcohol copolymers, vinylidene chloride polymer, acrylonitrile polymer, copolymers of acrylonitrile and methyl acrylate, semicrystalline polyesters, polyethylene terephthalate, polyamides, crystalline polymers, epoxy resins based on N,N-dimethylethylenediamine and resorcinol, polyurethane engineering thermoplastics, and combinations thereof.

15. A method according to claim 11, wherein the thermoplastic gas barrier polymer comprises an ethylene-vinyl alcohol copolymer.

16. A method according to claim 1, wherein the laminate membrane has at least one layer comprising an ethylene-vinyl alcohol copolymer and at least two layers comprising thermoplastic elastomer adjacent to the ethylene-vinyl alcohol copolymer layer, and wherein the annealing step (b) is carried out at one or more temperatures between an $\alpha$-transition temperature and a $\beta$-transition temperature of the ethylene-vinyl alcohol copolymer.

17. A method according to claim 16, wherein the laminate membrane has outer layers that are at least about 125 microns thick.

18. A method according to claim 1, wherein the laminate membrane has a layer of a microlayer polymeric composite, wherein the microlayer polymeric composite has alternating layers of at least one polymeric fluid barrier material and at least one thermoplastic elastomeric material.

19. A method according to claim 1, including a further step of forming the laminate membrane into a desired shape.

20. A method according to claim 19, wherein the laminate membrane is formed into the desired shape with heat.

21. A laminate membrane produced by the method of claim 1.

22. An inflated bladder, wherein said bladder is formed by sealing and inflating a laminate membrane according to claim 21.

23. An inflated bladder according to claim 22, wherein said bladder is inflated with gas comprising a member selected from the group consisting of air and nitrogen.

24. An article comprising a laminate membrane according to claim 21.

* * * * *

UNITED STATES PATENT AND TRADEMARK OFFICE
CERTIFICATE OF CORRECTION

PATENT NO. : 7,033,458 B2
APPLICATION NO. : 10/137531
DATED : April 25, 2006
INVENTOR(S) : Yihua Chang et al.

It is certified that error appears in the above-identified patent and that said Letters Patent is hereby corrected as shown below:

Column 10,
Line 60, "a" should be --α--.

Column 12,
Line 67, after "according" insert --to--.

Column 13,
Line 6, "steam" should be --stream--.

Column 18,
Line 41, claim 8, delete "during".

Line 64, claim 13, "form" should be --from--.

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 7,033,458 B2 Page 1 of 1
APPLICATION NO. : 10/137531
DATED : April 25, 2006
INVENTOR(S) : Yihua Chang et al.

It is certified that error appears in the above-identified patent and that said Letters Patent is hereby corrected as shown below:

Column 10,
Line 60, "a" should be --$\alpha$--.

Column 12,
Line 67, after "according" insert --to--.

Column 13,
Line 6, "steam" should be --stream--.

Column 18,
Line 41, claim 8, delete "during".

Line 64, claim 13, "form" should be --from--.

Signed and Sealed this

Seventeenth Day of October, 2006

JON W. DUDAS
*Director of the United States Patent and Trademark Office*